United States Patent
Kimchy et al.

(10) Patent No.: US 9,872,656 B2
(45) Date of Patent: *Jan. 23, 2018

(54) FAIL-SAFE RADIATION CONCEALMENT MECHANISMS FOR IMAGING CAPSULES

(71) Applicant: CHECK-CAP LTD., Isfiya (IL)

(72) Inventors: Yoav Kimchy, Haifa (IL); Rafi Sommer, Nesher (IL)

(73) Assignee: CHECK-CAP LTD., Isfiya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,345

(22) Filed: May 15, 2013

(65) Prior Publication Data

US 2014/0037069 A1     Feb. 6, 2014

Related U.S. Application Data

(60) Provisional application No. 61/647,215, filed on May 15, 2012, provisional application No. 61/647,234, filed on May 15, 2012.

(51) Int. Cl.
*A61B 6/00*     (2006.01)

(52) U.S. Cl.
CPC ............ *A61B 6/4057* (2013.01); *A61B 6/425* (2013.01); *A61B 6/4258* (2013.01)

(58) Field of Classification Search
None
See application file for complete search history.

(56) References Cited

U.S. PATENT DOCUMENTS

| | | | | |
|---|---|---|---|---|
| 4,262,271 A | * | 4/1981 | Bowers et al. | 335/263 |
| 4,708,062 A | * | 11/1987 | Bjork et al. | 102/420 |
| 6,442,799 B1 | * | 9/2002 | Duarte et al. | 16/277 |
| 8,068,897 B1 | * | 11/2011 | Gazdzinski | 600/476 |
| 2011/0152639 A1 | * | 6/2011 | Matott | 600/302 |
| 2013/0018491 A1 | * | 1/2013 | Kelly | G01N 1/2035 700/90 |

FOREIGN PATENT DOCUMENTS

IL     WO 2008096358 A2 * 8/2008     ........... A61B 6/4057

* cited by examiner

*Primary Examiner* — Patricia Park
*Assistant Examiner* — Nate S Sunwoo
(74) *Attorney, Agent, or Firm* — Soroker Agmon Nordman (57) ABSTRACT

An imaging capsule with a fail-safe radiation mechanism includes a first rotatable disk with a radiation source mounted thereon and having a collimator structure allowing emission of radiation from radiation source from a few locations on the first disk. A second rotatable disk surrounds the first disk, is rotatable relative to first disk, and includes areas that block radiation and areas that are transparent to emission of radiation. In a rest position, second disk is situated relative to first disk such that areas that block radiation are blocking the emission of radiation from the locations on the circumference of the disk that allow the emission of radiation. A motor is activated to rotate one of the disks and allow emission of radiation. A connector is configured to automatically return first disk and second disk to the rest position when the motor is deactivated.

12 Claims, 7 Drawing Sheets

FAIL-SAFE RADIATION CONCEALMENT MECHANISMS FOR IMAGING CAPSULES

CROSS-REFERENCE TO RELATED APPLICATIONS

This application claims the benefit of U.S. Provisional Patent Application No. 61/647,215, having a filing date of 15 May 2012, and U.S. Provisional Patent Application No. 61/647,234, having a filing date of 15 May 2012, both of which are incorporated herein by reference.

TECHNICAL FIELD

The present disclosure relates generally to limiting exposure of a patient to radiation and more specifically to a low-power-consumption, fail-safe radiation concealment mechanism in an imaging capsule that is swallowed by a patient to examine the patient's gastrointestinal tract.

BACKGROUND

One method for examining the gastrointestinal tract for the existence of polyps and other clinically relevant features that may indicate regarding the potential of cancer is performed by swallowing an imaging capsule that will travel through the tract and view the patient's situation. In a typical case the trip can take between 24-48 hours, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays or Gamma rays. The radiation is typically collimated to allow it to be controllably directed toward a specific area during the imaging process. In an exemplary case the imaging capsule is designed to measure Compton back-scattering and transmits the measurements (e.g. count rate) to an external analysis device, for example a computer or other dedicated instruments.

In a typical implementation a radio-opaque contrast agent is used so that a position with a polyp will have less contrast agent and will measure a larger back-scattering count. Alternatively, other methods may be used to image the gastrointestinal tract.

U.S. Pat. No. 7,787,926 to Kimchy the disclosure of which is incorporated herein by reference, describes details related to the manufacture and use of such an imaging capsule.

Use of an imaging capsule exposes the user to radiation, which may be potentially harmful. Accordingly, it is of interest to limit the user's exposure to radiation when not necessary, for example while the imaging capsule is located in positions that do not need to be measured. Typically, the imaging capsule may be designed with shutters that can be instructed to block the exit of radiation when not needed. However, there still exists the hazard that in case of malfunction of the imaging capsule, for example in case of a power failure, radiation may be emitted without constraint.

It is thus desirable to design a fail-safe radiation blocking mechanism that automatically blocks the emission of radiation and only allows radiation to be emitted if power is available and the device provides an instruction to allow radiation to be emitted. It may be further desirable to provide such a mechanism that can save power when opening and closing the shutters.

SUMMARY OF THE INVENTION

According to various aspects of the disclosure, an imaging capsule with a fail-safe radiation mechanism may include a first rotatable disk with the radiation source mounted thereon. The first disk has a collimator structure allowing the emission of radiation from the radiation source substantially only from a few locations on the circumference of the first disk. A second rotatable disk surrounds the circumference of the first rotatable disk and is configured to rotate relative to the first disk. The second disk includes areas that block radiation and areas that are transparent to the emission of radiation. In a rest position, the second disk is situated relative to the first disk such that the areas that block radiation are blocking the emission of radiation from the few locations on the circumference of the disk that allow the emission of radiation. A connector assembly couples the first disk to the second disk, and a motor rotates one of the rotatable disks relative to the other of the rotatable disks. The first disk and second disk are initially in the rest position blocking the emission of radiation until the motor is activated to rotate one of the rotatable disks and allow the emission of radiation. The connector is configured to automatically return the first disk and the second disk to the rest position when the motor is deactivated.

In some aspects, a method of providing fail-safe radiation while scanning inside a living body may include mounting a radiation source on a first rotatable disk, positioning collimators on the first rotatable disk so that the radiation is substantially allowed to be emitted only from a few locations on the circumference of the first rotatable disk, and placing a second rotatable disk to surround the circumference of the first rotatable disk and configured to rotate relative to the first rotatable disk, the second rotatable disk including areas that block radiation and areas that are transparent to the emission of radiation. The method further includes situating the second rotatable disk and the first rotatable disk initially in a rest position wherein the second rotatable disk is situated relative to the first rotatable disk such that the areas that block radiation are blocking the emission of radiation from the few locations on the circumference of the first rotatable disk that allow the emission of radiation, receiving instructions to begin emitting radiation, activating the motor to rotate the first rotatable disk relative to the second rotatable disk to a position that allows the emission of radiation, and coupling the first rotatable disk and the second rotatable disk so that they will return to the rest position automatically when the motor is deactivated.

This disclosure generally concerns the description of several possible fail-safe concealment mechanisms to limit the radiation exposure of patients to ionizing radiation such as x-rays, gamma rays, and beta emissions from a radio isotope that is used in an imaging capsule. The capsule is designed to be swallowed by the patient and travels through the Gastro Intestinal tract. An example of such a concealment mechanism is described in U.S. patent application Ser. No. 10/596,065, filed on the May 26, 2006, now U.S. Pat. No. 7,787,926, titled Intra Lumen Imaging Capsule, and PCT Publication No. WO 2012/035528, titled Fail-safe Radiation Concealment Mechanism, the disclosures of which are incorporated herein by reference.

The concealment mechanism is designed with shutters that are normally closed, effectively stopping the emitted radiation from the radiation source within the capsule to exit the capsule, thus reducing the exposure of the patient to ionizing radiation.

When the radiation is emitted and the collimator is moving and scanning, detectors (13) in FIGS. 1-4 detect X-ray Fluorescence and Compton scattering photons which are used for 3D imaging within the colon as described in U.S. patent application Ser. No. 10/596,065.

The described mechanisms open the shutters only when the capsule requires these photons (or beta electrons) for imaging the internal lumen of the gastro intestinal tract.

The requirement of fail-safe in the context of this invention means that the shutter mechanism cannot remain open and is dependent on electric power to be opened. Thus, if there is no battery power for whatever reason, the shutters close and exposure to the patient is effectively stopped. In addition, if for any reason there is a leak of the oil in the concealment mechanism, the shutter mechanism will remain closed.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Reference will now be made in detail to specific embodiments or features, examples of which are illustrated in the accompanying drawings. Generally, corresponding or similar reference numbers will be used, when possible, throughout the drawings to refer to the same or corresponding parts.

Figure 1A:
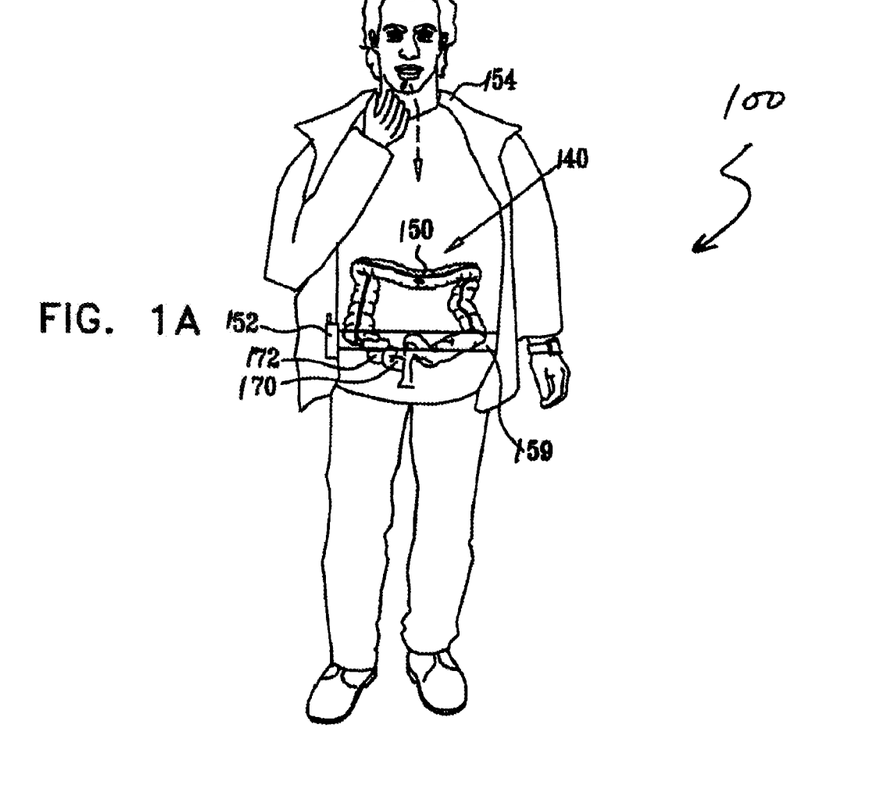
FIG. 1A is a schematic illustration of an exemplary screening system in accordance with various aspects of the disclosure.

Reference is made to FIG. 1A, which is a schematic illustration of a screening system 140, in accordance with various aspects of the disclosure. The system 140 typically comprises an ingestible capsule 150 and an external data-recording unit 152. For some applications, the data-recording unit 152 (FIG. 1B) may be worn on the waist of a subject 154 (as shown in FIG. 1A) or elsewhere on the subject's body, such as the wrist (configuration not shown), etc. Alternatively, for some applications, the capsule 150 may comprise an internal data-recording unit, and the external data-recording unit 152 may not be provided. In these applications, the data recorded by the capsule 150 is retrieved after the capsule has been expelled from the body.

During a typical screening procedure using system 140, an oral contrast agent 170 is administered to subject 154. Contrast agent 170 is typically adapted to pass through a gastrointestinal (GI) tract 172 and be expelled with the feces, substantially without being absorbed into the blood stream. The contrast agent material may be similar to compounds used routinely for the study of the GI with X-rays, such as Barium sulfate liquid concentrate, iodine-based compounds, or other such materials. For some applications, additional appropriate contrast agents include Tantalum, Gadolinium, Thorium, Bismuth, and compounds of these materials. After the contrast agent is administered (e.g., several hours after the contrast agent is administered), subject 154 swallows capsule 150.

Figure 2:
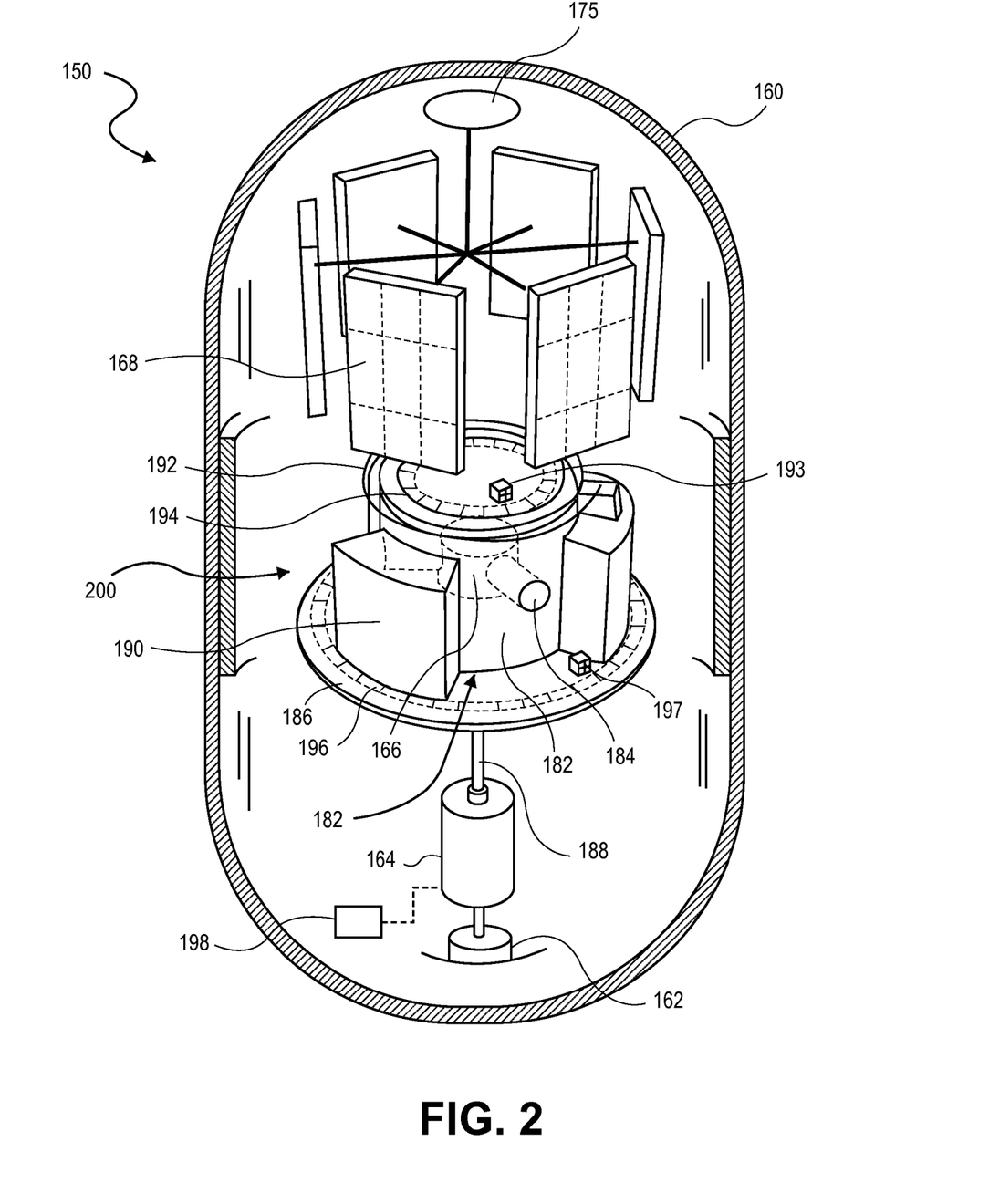
FIG. 2 is an illustration of an exemplary fail-safe imaging capsule according to various aspects of the disclosure.

Capsule 150 travels through GI tract 172, emitting gamma and/or X-ray radiation. Beginning at a certain point in time, capsule 150 records the Compton scattered gamma and/or X-ray photons that strike one or more radiation detectors 162 (FIG. 2). The count rate information received from each of the radiation detectors is typically stored together with a time stamp for that measurement. Within a time period typically of less than one second (e.g., several tens to several hundred milliseconds), it is assumed that the capsule and the surrounding colon wall and the contrast agent are in quasi-steady state. Taking small enough time intervals and integrating the counts over the small intervals allows for this quasi-steady-state assumption. The data may be stored in the capsule and sent by the capsule to the external recording unit from time to time, or after data-gathering has been completed.

Figure 1B:
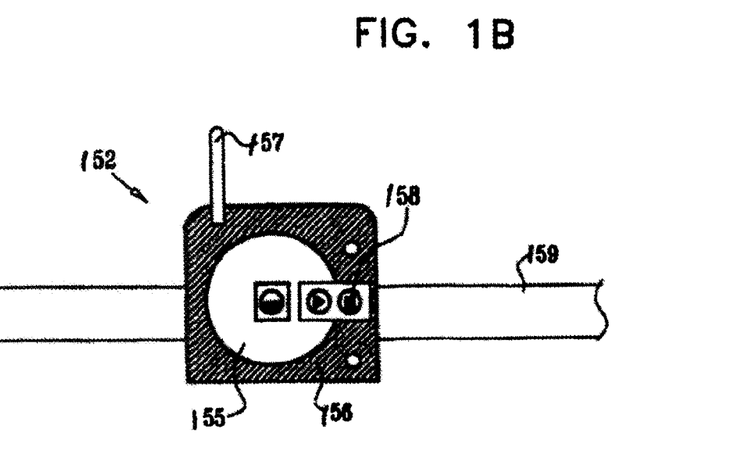
FIG. 1B is a schematic illustration of an exemplary external data-recording unit of the system of FIG. 1A in accordance with various aspects of the disclosure.

Reference is now made to FIG. 1B, which is a schematic illustration of the external data-recording unit 152, in accordance with an exemplary embodiment of the present disclosure. The data-recording unit 152 may comprise a receiver/memory unit 155, a support electronics/battery unit 156, an antenna 157, and/or user controls 158. In some aspects, the unit 152 may also include a strap 159, such as a belt or wrist/arm strap, for coupling the unit to the subject 154.

Reference is now made to FIG. 2, which is a schematic illustration of a perspective view of an exemplary failsafe imaging capsule 150, according to various aspects of the disclosure. In an exemplary embodiment of the invention, imaging capsule 150 is designed to automatically block radiation from being emitted from it until receiving instructions to release radiation and image its surroundings. In an exemplary embodiment of the invention, power is required to prevent blocking emission of radiation. Optionally, if imaging capsule 150 lacks power the radiation will be blocked.

In an exemplary embodiment, imaging capsule 150 includes an encasement 160 for holding and protecting the elements of the device from acids and other liquids or gases along its path of motion. Optionally, the encasement 160 should be able to withstand external pressures for at least 50-100 hours to allow for imaging capsule 150 to traverse the gastrointestinal tract and exit while still intact. Inside encasement 160, imaging capsule 150 includes a power source 162 (e.g. one or more batteries), a motor 164, a radiation source 166, one or more detectors 168, and a transceiver 175. In an exemplary embodiment of the invention, radiation source 166 is located on a first rotatable disk 180 and provides radiation that is blocked by a filling material 182 that forms a portion of the first disk 180. For example, the filling materials may be made of lead or tungsten or other dense materials. Optionally, the radiation is only free to travel in a few specific directions through one or more collimators 184 formed in the first disk 180.

In an exemplary embodiment, power source 162 provides power to motor 164, and motor 164 is rigidly and operably coupled to a second rotatable disk 186. The second rotatable disk 186 is rotatable relative to the first rotatable disk 180. Both the first and second rotatable disks 180, 186 are rotatable about the same rotation axis 188. One or more directed radiation beams may be emitted from collimators 184 controllably scanning the surroundings through the imaging capsule 150. One or more detectors 168 can detect backscattered particles resulting from the directed radiation beam. In an exemplary embodiment, detector(s) 168 may count the detected particle and provides the information to transceiver 175 for transmission to an external data recording unit 152 (e.g., a computer or processor) for processing and optionally constructing a visual representation of the information. In some embodiments of the invention, transceiver 175 uses radio frequency (RF) transmissions to receive instructions from an external device (unit 152 or another) and to provide information to the external device (unit 152 or another). In some aspects, the external device may instruct imaging capsule 150 to start scanning, to stop scanning, to scan in a specific motion pattern, to scan at specific times, etc.

In an exemplary embodiment, a radiation concealment mechanism 200 may include the first rotatable disk 180 and the second rotatable disk 186 that share the same rotation axis 188. The first rotatable disk 180 and is free to rotate relative to the second rotatable disk 186. The second disk 186 includes shutters or blocking areas 190 coupled therewith, which are made up from a material that blocks radiation. In an initial rest position, second rotatable disk 186 is positioned so that shutters 190 coincide and align with the outlets of collimators 184, so that the emission of radiation from the collimators 184 is blocked.

In an exemplary embodiment of the invention, the first rotatable disk 180 and the second rotatable disk 186 are connected together with a spring 192, for example, in the shape of a spiral. Thus, if the second rotatable disk 186 is rotated, for example, clockwise, the spring will tighten and exert a force on the first rotatable disk 180, so that the first rotatable disk 180 will aspire to follow suit and rotate clockwise also.

It should be appreciated that as the second rotatable disk 186 rotates relative to the first rotatable disk 180, in some positions, shutters 190 stop blocking the outlets of collimators 184 and the radiation is freely emitted to scan the patient. In the rest position of radiation control mechanism 200, spring 192 is unwound (i.e., unloaded) and the collimators 184 are blocked. After rotating the second rotatable disk 186 some amount relative to the first rotatable disk 180, the spring 192 is in a tightened (i.e., loaded) configuration. Thus, any relative angular (rotational) movement between the first rotatable disk 180 and the second rotatable disk 186 is quickly corrected since this relative angular movement loads the spring 192 and the spring 192 in turn reacts to return the relative angular position back to the rest position.

To activate the concealment mechanism 200, the electric motor 164 is energized. The motor 164 performs a swift movement of large angular rotation in one direction (e.g., clockwise) and stops. This swift turn of the motor 164 rotates the second rotatable disk 186 relative to the first rotatable disk 180 since the second rotatable disk 186 is fixedly coupled for rotation by the motor 164. This relative rotation between the first rotatable disk 180 and the second rotatable disk 186 loads the spiral spring 192. Since the shutters 190 are rigidly coupled with the second rotatable disk 186, this swift angular turn exposes the collimators 184 of the first rotatable disk 180 and the radiation is freely emitted to scan the patient.

Once the motor 164 stops, the loaded spiral spring 192 urges the the first rotatable disk 180 to rotate relative to the second rotatable disk 186. As the first rotatable disk 180 turns relative to the second rotatable disk 186, the spring 192 is unloaded. At this time, the first rotatable disk 180 accelerates rotationally while the spiral spring 192 pulls the first rotatable disk 180 towards the equilibrium point relative to the second rotatable disk 186. At the equilibrium point (i.e., rest position), the collimators 184 are aligned just behind the shutters 190 of the second rotatable disk 186. All the time until collimators 184 are aligned behind the shutters 190 of the second rotatable disk 186, the collimators are open and thus radiation, for example, x-rays, gamma rays, or the like are emitted. Once the collimators 184 are aligned behind the shutters 190 of the second rotatable disk 186, the x-rays, gamma rays, or the like are blocked.

When the motor 164 stops and the loaded spring 192 urges the first rotatable disk 180 to rotate relative to the second rotatable disk 186, the first rotatable disk 180 accelerates rotationally and acquires and angular (rotational) velocity and momentum. Thus, in the absence of a rotationally stopper, the first rotatable disk 180 rotates relative to the second rotatable disk 186 until it overshoots the equilibrium point, and the collimators 184 are covered and then again uncovered by the shutters 180 as they overshoot. This overshoot in turn again starts to load the spiral spring 192, this time in an opposite angular direction compared with the initial loading of the spring 192. Thus, the resistance of the spring 192 to the reloading thus slows down the rotation of the first rotatable disk 180 relative to the second rotatable disk 186 until the relative rotation stops and starts to return the first and second rotatable disks 180, 186 back to the equilibrium position where the collimators 184 are behind the shutters 180.

It should be understood that this mechanical behavior can be described using the general equation of a driven spring and mass rotating harmonic mechanical oscillator. The first and second rotatable disks 180, 186 are attached to one another with a spring 192. This mechanical structure can be viewed as a driven mechanical oscillator where the first rotatable disk 180 is free to move about its central axis 188 and is tied by a spring 192 with its mass M. The second rotatable disk 186 is rigidly connected to the electric motor 164.

To activate the concealment mechanism, the electric motor 164 is energized. The motor 164 performs a swift movement of large angular rotation in one direction and stops. A first encoder ring 194 is connected to the first rotatable disk 180 and second encoder ring 196 is connected to the second rotatable disk 182. A controller 198 is connected to a first encoding sensor 193, which detects encoder ring 194, and to a second encoding sensor 197, which detects encoder ring 196. The sensors 193, 197 count the number of sectors that the first rotatable disk 180 and the second rotatable disk 182 rotate. This enables the controller 198 to know when the collimators 184 get behind the shutters 190 of the second rotatable disk 182. Thus, the controller 198 can selectively activate the electric motor 164 when it is desired to uncover the collimators 184 to radiate the patient.

The controller 198 can thus activate the electric motor 164 to short periods of time acting as a driver to the forced mechanical oscillator that is comprised of the first rotatable disk 180 and the second rotatable disk 182 attached with a spring 192. Every short motor movement drives this mechanical system to oscillate. Thus applying electric motor 164 drive only at the correct timing in accordance with the relative position of the first and second encoder rings 194, 196, the controller 198 activates the electric motor 164 to move in a back and forth rotational direction in sync with the natural harmonic frequency of the mechanical oscillating system using the information of the encoder sensors 193, 197 to coordinate the activation times of the motor 164, as well as advancing the relative position of the shutters 190 so that over time there are no blind spots for the scanning.

Figure 3:
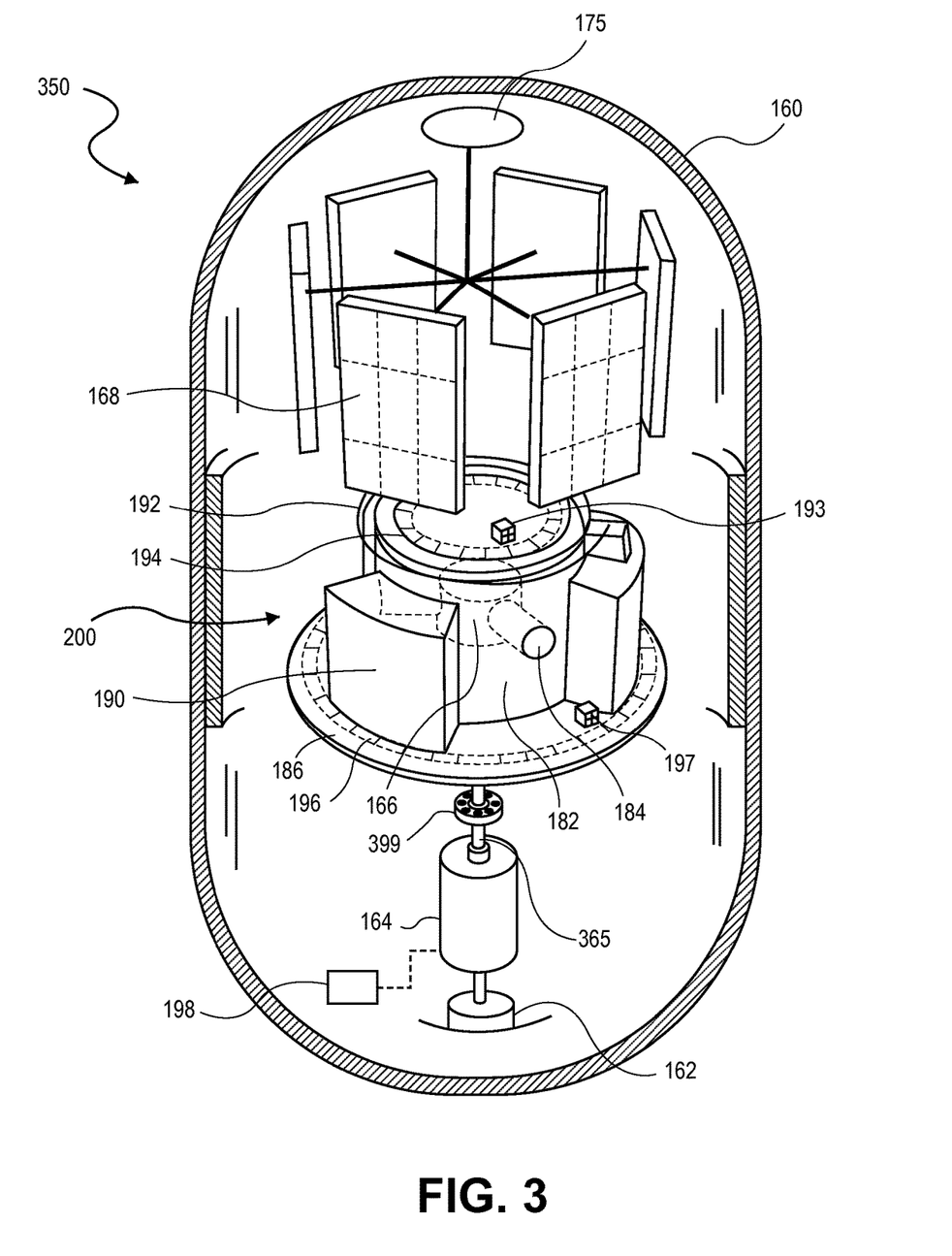
FIG. 3 is an illustration of an exemplary fail-safe imaging capsule according to various aspects of the disclosure.

Referring now to FIG. 3, according to various aspects, an exemplary imaging capsule 350 similar to the previously-described capsule 150 may include the electric motor 164 and the second rotatable disk 186, which are rigidly connected together. The imaging capsule 350 includes a one directional bearing 399 operably coupled with a drive shaft 365 of the electric motor 164 to ensure that the second rotatable disk 186 does not turn backwards when the electric motor 164 is not powered. In this case, all motor movements are in the same rotational direction and not back and forth. The controller 198 activates the electric motor to move in one direction in sync with the natural harmonic frequency of the mechanical oscillating system.

Figure 4:
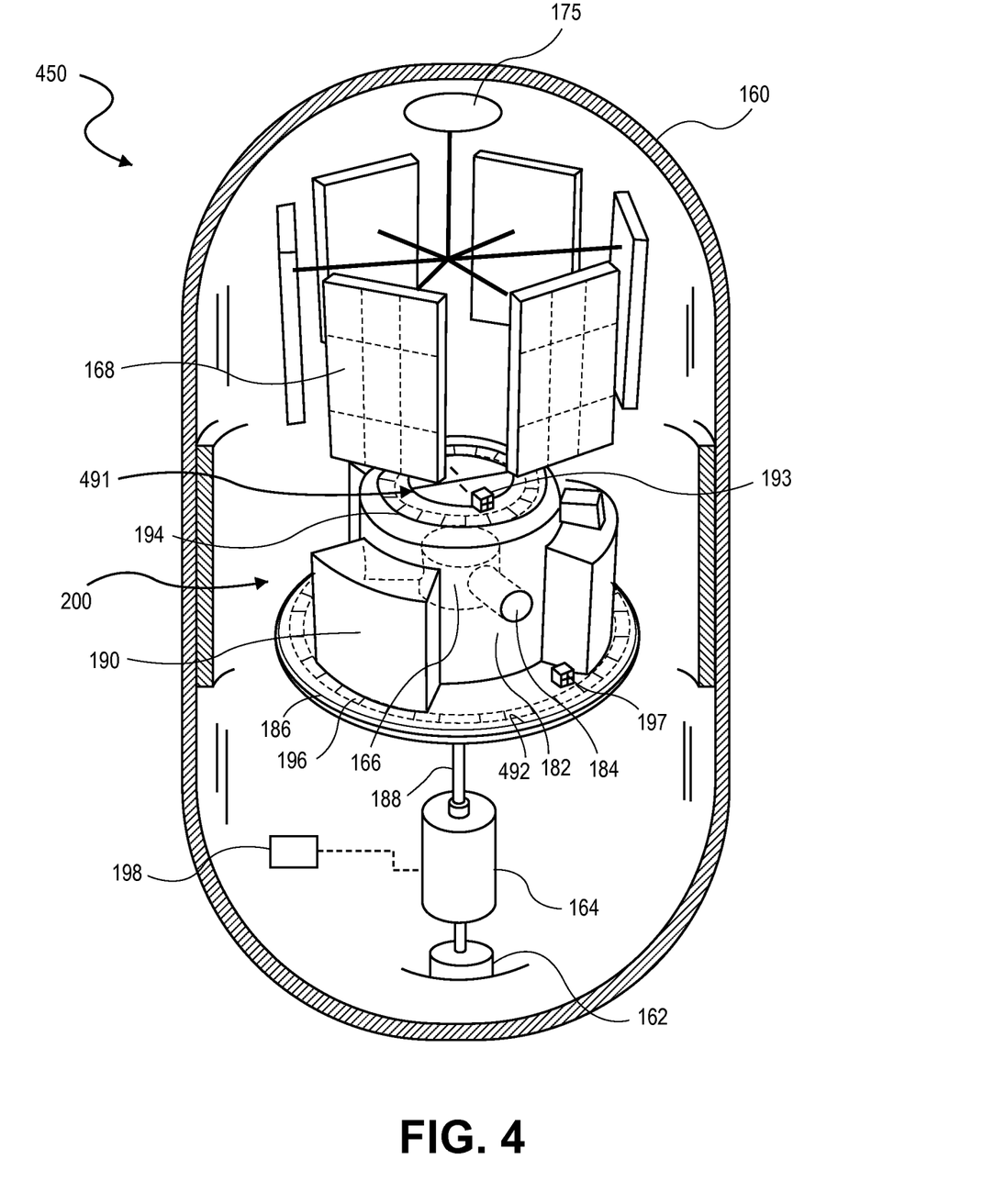
FIG. 4 is an illustration of an exemplary fail-safe imaging capsule according to various aspects of the disclosure.

Referring now to FIG. 4, in another embodiment of an exemplary imaging capsule 450 similar to capsule 150 described above, the spiral spring 192 of the embodiments of FIGS. 2 and 3 is replaced by a pair of magnetic rings 491, 492. The first magnetic ring 491 is fixedly coupled with the first rotatable disk 180, and the second magnetic ring 492 is fixedly coupled with the second rotatable disk 186. The magnets 491, 492 operate to "connect" the first rotatable disk 180 and the second rotatable disk 186 as did the spiral spring 192 in the previous embodiments. For example, the magnets 491, 492 exert a "reverse" rotational torque as similar poles are moved toward a position facing each other and exert a "forward" rotational torque as opposite poles are moved toward a position facing each other.

Figure 5:
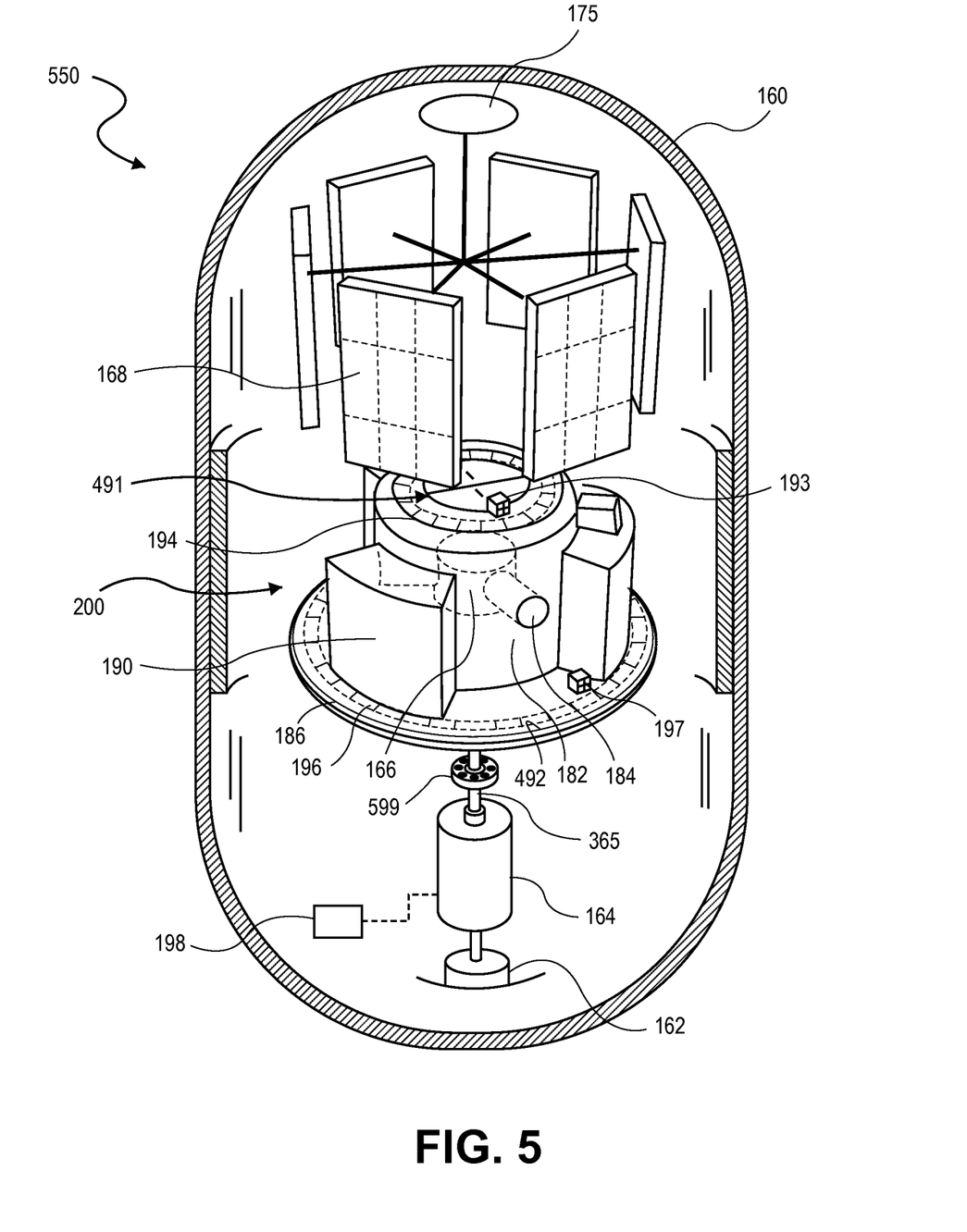
FIG. 5 is an illustration of an exemplary fail-safe imaging capsule according to various aspects of the disclosure.

Referring now to FIG. 5, according to various aspects, an exemplary imaging capsule 550 similar to the previously-described capsule 450 may include the electric motor 164 and the second rotatable disk 186, which are rigidly connected together. The imaging capsule 550 includes a one directional bearing 599 operably coupled with a drive shaft 365 of the electric motor 164 to ensure that the second rotatable disk 186 does not turn backwards when the electric motor 164 is not powered. In this case, all motor movements are in the same rotational direction and not back and forth. According to an exemplary embodiment of this disclosure, the shutter mechanism depends on fluid dynamic friction force to open and closes when rotation stops.

Figure 6:
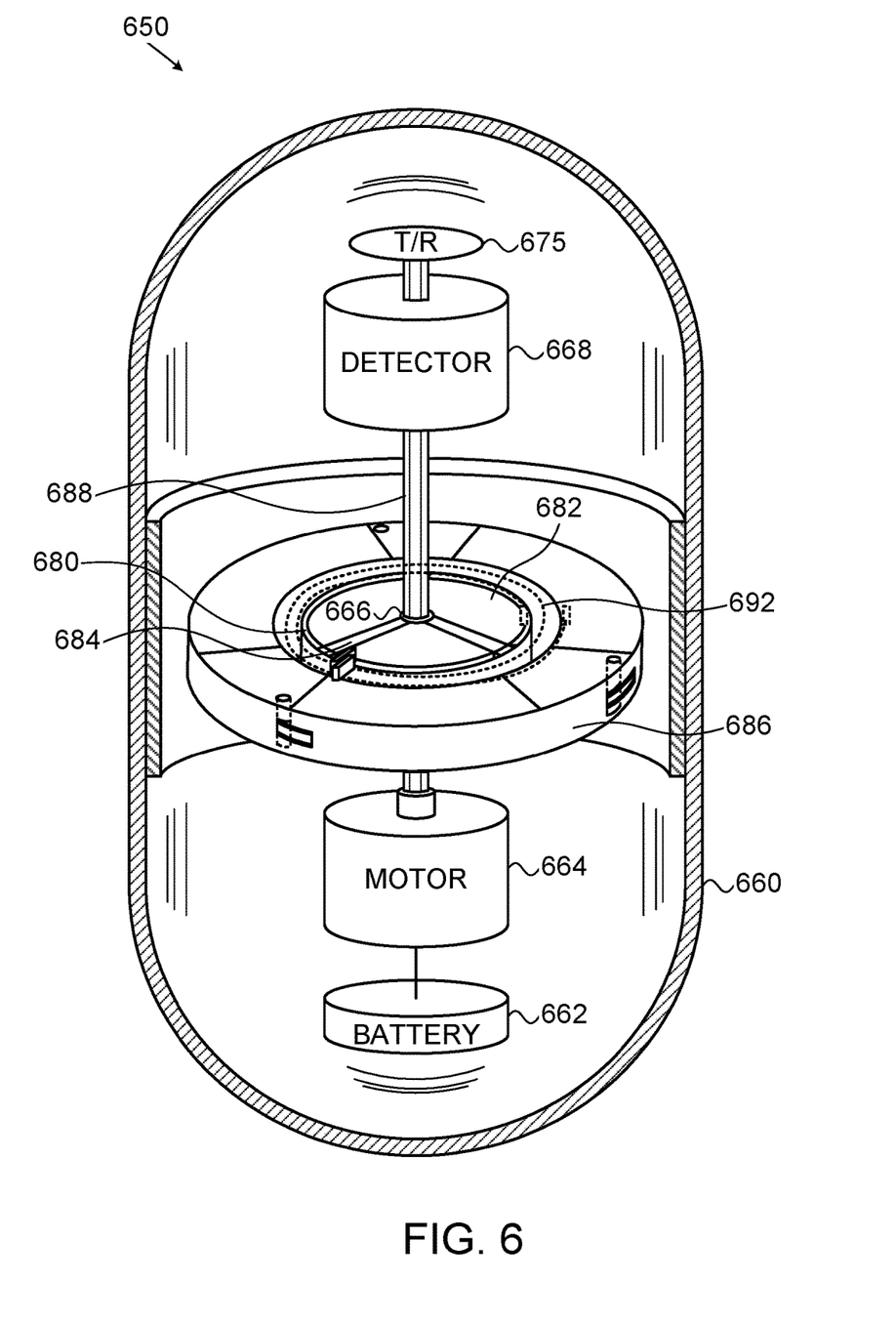
FIG. 6 is an illustration of an exemplary fail-safe imaging capsule according to various aspects of the disclosure.
Figure 7:
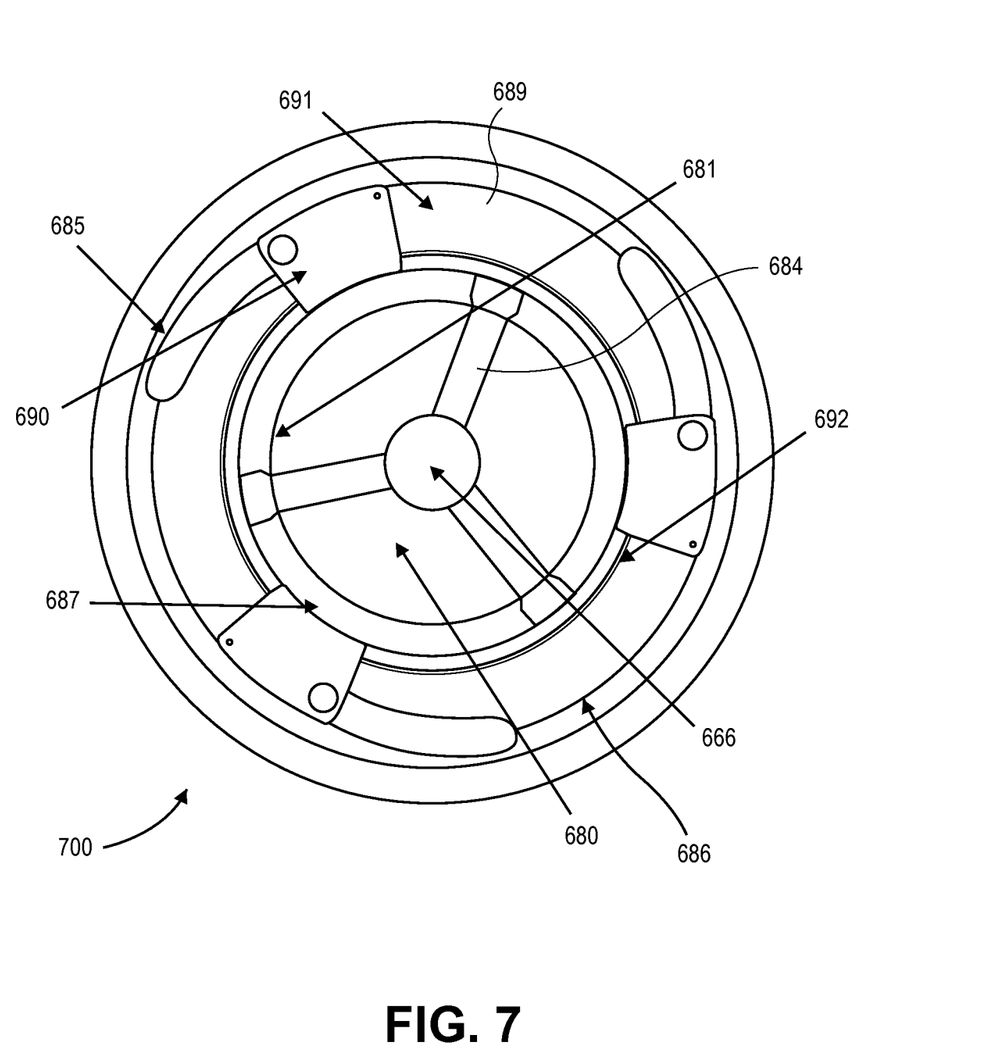
FIG. 7 is a cross-sectional view of an exemplary fail-safe concealment assembly of the fail-safe imaging capsule of FIG. 6.

FIGS. 6 and 7 illustrate an exemplary embodiment of a fail-safe mechanism that is based on the following principle of operation. An exemplary imaging capsule 650 is designed to automatically block radiation from being emitted from it until receiving instructions to release radiation and image its surroundings. In an exemplary embodiment of the invention, power is required to prevent blocking emission of radiation. Thus, if imaging capsule 650 lacks power the radiation will be blocked.

In an exemplary embodiment, imaging capsule 650 includes an encasement 660 for holding and protecting the elements of the device from acids and other liquids or gases along its path of motion. Inside encasement 660, imaging capsule 650 includes a power source 662 (e.g. one or more batteries), a motor 664, a radiation source 666, one or more detectors 668, and a transceiver 675. In an exemplary embodiment of the invention, radiation source 666 is located on a first rotatable disk 680 and provides radiation that is blocked by a filling material 682 that forms a portion of the first disk 680. For example, the filling materials may be made of lead or tungsten or other dense materials. Optionally, the radiation is only free to travel in a few specific directions through one or more collimators 684 formed in the first disk 680.

In an exemplary embodiment, power source 662 provides power to motor 664, and motor 664 is rigidly and operably coupled to the first rotatable disk 680. A second rotatable disk 686 is mounted for rotation relative to the first rotatable disk 680. Both the first and second rotatable disks 680, 686 are rotatable about the same rotation axis 688. One or more directed radiation beams may be emitted from collimators 684 controllably scanning the surroundings through the imaging capsule 650. One or more detectors 668 can detect backscattered particles resulting from the directed radiation beam. In an exemplary embodiment, detector(s) 668 may count the detected particle and provides the information to transceiver 675 for transmission to an external data recording unit 152 (e.g., a computer or processor) for processing and optionally constructing a visual representation of the information. In some embodiments, transceiver 675 uses radio frequency (RF) transmissions to receive instructions from an external device (unit 152 or another) and to provide information to the external device (unit 152 or another). In some aspects, the external device may instruct imaging capsule 650 to start scanning, to stop scanning, to scan in a specific motion pattern, to scan at specific times, etc.

Referring now to FIG. 7, in an exemplary embodiment, a radiation concealment mechanism 700 may include the first rotatable disk 680 and the second rotatable disk 686 that share the same rotation axis 688. The first rotatable disk 680 may include a first limiter 681 fixed thereto, and the second rotatable disk 686 may include a second limiter 687 fixed thereto. The second rotatable disk 686 and is free to rotate relative to the first rotatable disk 680. The second disk 686 includes shutters or blocking areas 690 coupled therewith, which are made up from a material that blocks radiation. The shutters 690 are movable in a chamber 689 containing a viscous liquid 691. In an initial rest position, second rotatable disk 686 is positioned so that shutters 690 coincide and align with the outlets of collimators 684, so that the emission of radiation from the collimators 684 is blocked.

In an exemplary embodiment of the invention, the first rotatable disk 680 and the second rotatable disk 686 are connected together with a spring 692, for example, in the shape of a spiral. Thus, if the first rotatable disk 680 is rotated, for example, clockwise, the spring 692 will tighten (i.e., load) and exert a force on the second rotatable disk 686, so that the second rotatable disk 686 will aspire to follow suit and rotate clockwise also. Although the second rotatable disk 686 wants to turn relative to the first rotatable disk 680 under the urging of the loaded spring 692, the second rotatable disk 686 moves in the viscous liquid 691, which in turn exerts torque on the second rotatable disk 686 and pivotable fins 685 to resist movement of the second rotatable disk 686 relative to the first rotatable disk 680.

Rotation of the first rotatable disk 680 by the motor 664, for example, in the clockwise direction as viewed in FIG. 7, changes the position of the first rotatable disk 680 relative to the second rotatable disk 686 until the first position limiter 681 reaches the second position limiter 687 at an open configuration. Once the first position limiter 681 reaches the second position limiter 687, the first rotatable disk 680 and the second rotatable disk 686 turn together, whereby the spring 692 connecting between the first and second disks 680, 686 is loaded. At this position, the first rotatable disk 680 and the second rotatable disk 686 are aligned so that radiation from the radiation source 666 can escape through the collimators 684, which are no longer blocked by the shutters 690. This continues as long as the motor 664 rotates the first rotatable disk 680 at sufficient rotational velocity to keep the spring 692 loaded at the open configuration of the first and second limiters 681, 687.

When the motor 664 stops turning the first rotatable disk 680, the torque induced by the viscous liquid 691 is reduced. Thus, the loaded spring 692 exerts torque that exceeds any torque induced by the viscous liquid 691 and moves the second rotatable disk 686 until the second limiter 687 of the second rotatable disk 686 reaches the first limiter 681 at a closed configuration. At this closed configuration, the shutters 690 block radiation from escaping the collimators 684. The spring 692 is preloaded so that it holds the first rotatable disk 680 and the second rotatable disk 686 in this closed configuration absent energization of the motor, preventing movements between the first rotatable disk 680 and the second rotatable disk 686, and thus blocking radiation by the radiation source 666 from escaping via the collimators 684.

It should be appreciated that the spring 692 can be replaced by other types of flexible material which will exert torque when displaced. In another embodiment, magnets can be placed instead of the spring 692 to exert torque if brought close together (similar poles facing each other) or exert torque pulling each other (opposite poles facing each other).

It should be understood by persons skilled in the art that the viscosity of the liquid or gel 691 may be chosen according to the required rotational velocity of the concealment mechanism 700. If a fast rotational velocity is chosen, a low viscosity liquid will generate sufficient drag to load the spring 692 at high rotational velocity. If a slow rotational velocity is chosen for the concealment mechanism 700, a high viscosity liquid or gel is required to generate sufficient drag to load spring 692 at low rotational speed.

The viscous liquid 691 can be Paraffin oil if low viscosity liquid is chosen or other bio compatible high viscosity liquid or gel such that if a leak occurs and liquid or gel is released out of the capsule into the gastro intestinal track, it will not cause any harm. In this scenario, if the liquid escapes the capsule, the concealment mechanism 700 will not function and will not open as it will not exert torque on the second rotatable disk 686 when turning. This constitutes a safety feature of this concealment mechanism keeping it closed and blocking radiation from escaping if the mechanical integrity of the concealment mechanism is compromised.

In another embodiment, the viscous liquid or gel 691 is contained in a sealed container that is positioned near the concealment mechanism 700. On the concealment mechanism 700, at least one magnet may be attached. Inside the sealed container with the viscous liquid or gel, at least one fin 685 made of magnetic material or ferromagnetic material is placed such that when the concealment mechanism 700 rotates, this fin 685 rotates with the concealment mechanism due to its attraction to the at least one magnet on the concealment mechanism.

In another embodiment of this invention, ferromagnetic or magnetic powder is placed in the sealed container with the viscous liquid or gel. This powder is attracted to the at least one magnet on the concealment mechanism and rotates when the concealment mechanism rotates. This powder acts in the same manner as the fin described above.

It should be appreciated that the radiation source 160 may be adapted to emit gamma rays, X-rays, and/or beta electrons (i.e., radiation having an energy of at least 10 keV). For some applications, the radiation source 166, 666 may comprise a radioisotope or a miniature radiation generator. In some aspects of the disclosure, radiation source 166, 666 may comprise a miniature X-ray generator, such as those described in one or more of the following references: U.S. Pat. Nos. 6,134,300 and 6,353,658 to Trebes et al.; Haga, A. et al., "A miniature x-ray tube," Applied Physics Letters 84(12):2208-2210 (2004); and Gutman, G. et al., "A novel needle-based miniature x-ray generating system," Phys Med Biol 49:4677-4688 (2004). Such a miniature X-ray generator or X-ray tube may be used for radiation source 160 instead of a radioisotope to illuminate the colon contents with X-ray photons. Turning such a generator on and off as needed typically reduces exposure of the subject to radiation. In addition, the energy range can be better controlled and the flux may be higher for the on periods without increasing subject total exposure. It should be appreciated that the capsule 150, 350, 450, 550, 650 may include more than one radiation source 166, 666. According to various aspects, the capsule 150, 350, 450, 550, 650 may comprise one or more gamma and/or X-ray radiation sources and/or sources of beta electrons, such as T1201, Xe133, Hg197, Yb169, Ga67, Tc99, Tc99m, In111, I131 or Pd100.

The capsule 150, 350, 450, 550, 650 also typically comprises circuitry (not shown), which, for some applications, may include a pressure sensor. In an embodiment of the disclosure, the radiation source 166, 666 and detector(s) 168, 668 are arranged to "observe" the entire 4 pi squared sphere (or a portion of it) surrounding the capsule.

From the foregoing, it will be appreciated that, although specific embodiments have been described herein for purposes of illustration, various modifications or variations may be made without deviating from the spirit or scope of inventive features claimed herein. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

What is claimed is:

1. An imaging capsule with a fail-safe radiation mechanism, comprising:
    a radiation source;
    a first rotatable disk with the radiation source mounted thereon, the first rotatable disk having a collimator structure allowing the emission of radiation from the radiation source from one or more locations on the circumference of the first disk;
    a second rotatable disk surrounding the circumference of the first rotatable disk and configured to rotate relative to the first rotatable disk, the second rotatable disk including areas that block radiation and areas that are transparent to the emission of radiation, wherein the areas that block radiation on the second rotatable disk are located so that there exists a rest position of the second rotatable disk relative to the first rotatable disk in which the areas that block radiation on the second rotatable disk coincide with the one or more locations on the circumference of the first rotatable disk that allow the emission of radiation, to block the emission of radiation;
    a connector assembly configured to couple the first rotatable disk to the second rotatable disk: and
    a motor for rotating one of the rotatable disks relative to the other of the rotatable disks,
    wherein the first rotatable disk and second rotatable disk are configured to be initially in the rest position blocking the emission of radiation until the motor is activated to rotate the one of the rotatable disks and allow die emission of radiation, and wherein the connector assembly is configured to automatically return the first rotatable disk and the second rotatable disk to the rest position when the motor is deactivated, thus providing a fail-safe radiation mechanism.

2. An imaging capsule according to claim 1, wherein the connector assembly comprises a spring.

3. An imaging capsule according to claim 1, wherein the, connector assembly comprises a magnetic assembly.

4. An imaging capsule according to claim 3, wherein the magnetic assembly comprises a first magnet fixedly coupled with the first rotatable disk and a second magnet fixedly coupled with the second rotatable disk.

5. An imaging capsule according to claim 2, further comprising a first limiter attached to the first rotatable disk and a second limiter attached to the second rotatable disk, wherein the limiters prevent the first rotatable disk and second rotatable disk from leaving the rest position under the influence of the spring, and the limiters force the second rotatable disk to rotate with the first rotatable disk under the force of the motor.

6. An imaging capsule according to claim 1, wherein the first rotatable disk and the second rotatable disk are configured to controllably emit radiation 360 degrees around the rotatable disk.

7. An imaging capsule according to claim 1, wherein the first rotatable disk and the second rotatable disk are configured to controllably emit radiation for a pre-selected amount of time or a pre-selected number of rotations.

8. An imaging capsule according to claim 1, farther comprising a transceiver to receive instructions to activate or deactivate the motor.

9. An imaging capsule according to claim 1, wherein the imaging capsule is preprogrammed to activate or deactivate the motor at specific times.

10. An imaging capsule according to claim 1, wherein the second rotatable disk includes at least one chamber containing a viscous fluid, the viscous fluid causing a desired torque that counteracts a force of the connector assembly to prevent relative rotation between the first rotatable disk and the second rotatable disk.

11. A method of providing fail-safe radiation while scanning inside a living body, comprising:
mounting a radiation source on a first rotatable disk;
positioning collimators on the first rotatable disk so that the radiation is allowed to be emitted from one or more locations on the circumference of the first rotatable disk;
placing a second rotatable disk to surround the circumference of the first rotatable, disk and configured to rotate relative to the first rotatable disk, the second rotatable disk including areas that block radiation and areas that are transparent to the emission of radiation;
situating the second rotatable disk and the first rotatable disk initially in a rest position in which the locations of the areas that block radiation on the second rotatable disk coincide with the one or more locations on the circumference of the first rotatable disk that allow the emission of radiation, to block the emission of radiation;
receiving instructions to begin emitting radiation:
activating a motor to rotate the first rotatable disk relative to the second rotatable disk to a position that allows the emission of radiation: and
coupling the first rotatable disk and the second rotatable disk so that they will return to the rest position automatically when the motor is deactivated.

12. An imaging capsule according to claim 1, further comprising one or more detectors that detect backscattered particles resulting from the emission of radiation by the radiation source.

* * * * *